US010669153B2

(12) United States Patent
Holmes et al.

(10) Patent No.: US 10,669,153 B2
(45) Date of Patent: Jun. 2, 2020

(54) NEURO-CHEMICAL SENSOR WITH SELECTIVELY PERMEABLE MEMBRANE ON NANO-ELECTRODE

(71) Applicant: INTERNATIONAL BUSINESS MACHINES CORPORATION, Armonk, NY (US)

(72) Inventors: Steven J. Holmes, Yorktown Heights, NY (US); Emily R. Kinser, Poughkeepsie, NY (US); Qinghuang Lin, Yorktown Heights, NY (US); Nathan P. Marchack, New York, NY (US); Roy R. Yu, Poughkeepsie, NY (US)

(73) Assignee: International Business Machines Corporation, Armonk, NY (US)

( * ) Notice: Subject to any disclaimer, the term of this patent is extended or adjusted under 35 U.S.C. 154(b) by 446 days.

(21) Appl. No.: 15/602,332

(22) Filed: May 23, 2017

(65) Prior Publication Data

US 2018/0340203 A1    Nov. 29, 2018

(51) Int. Cl.
  *G01N 27/327*  (2006.01)
  *B82Y 15/00*   (2011.01)
  *C12Q 1/00*    (2006.01)
  *B82Y 40/00*   (2011.01)
  *C12Q 1/26*    (2006.01)

(52) U.S. Cl.
  CPC ........... *B82Y 15/00* (2013.01); *B82Y 40/00* (2013.01); *C12Q 1/005* (2013.01); *G01N 27/327* (2013.01); *G01N 27/3271* (2013.01); *C12Q 1/26* (2013.01); *C12Y 104/03011* (2013.01); *G01N 2333/90638* (2013.01); *G01N 2610/00* (2013.01)

(58) Field of Classification Search
  CPC .... B82Y 15/00; B82Y 40/00; G01N 27/3271; G01N 2610/00; G01N 2333/90638; G01N 27/327; C12Q 1/005; C12Q 1/26; C12Y 104/03011
  See application file for complete search history.

(56) References Cited

FOREIGN PATENT DOCUMENTS

WO      2004/060297 A2    7/2004
WO   WO-2007050100 A2 *   5/2007  ............... C12N 9/54

OTHER PUBLICATIONS

I. Gorelikov and N. Matsuura, "Single-Step Coating of Mesoporous Silica on Cetyltrimethyl Ammonium Bromide-Capped Nanoparticles" Nano Letters, 8(1), p. 369-373+S1-S3, Jan. (Year: 2008).*
Ghazaryan, L. et al., "Nanoporous SiO2 thin films made by atomic layer deposition and atomic etching" Nanotechnology (May 2016) pp. 1-9, vol. 27.

* cited by examiner

*Primary Examiner* — J. Christopher Ball
(74) *Attorney, Agent, or Firm* — Tutunjian & Bitetto, P.C.; L. Jeffrey Kelly

(57) ABSTRACT

A biosensor includes an array of electrically conductive nanorods formed on a substrate. The nanorods each includes a nanoscale porous coating formed on a surface of the nanorods from silicon dioxide layers. An enzyme coating is bound to the porous coating.

10 Claims, 8 Drawing Sheets

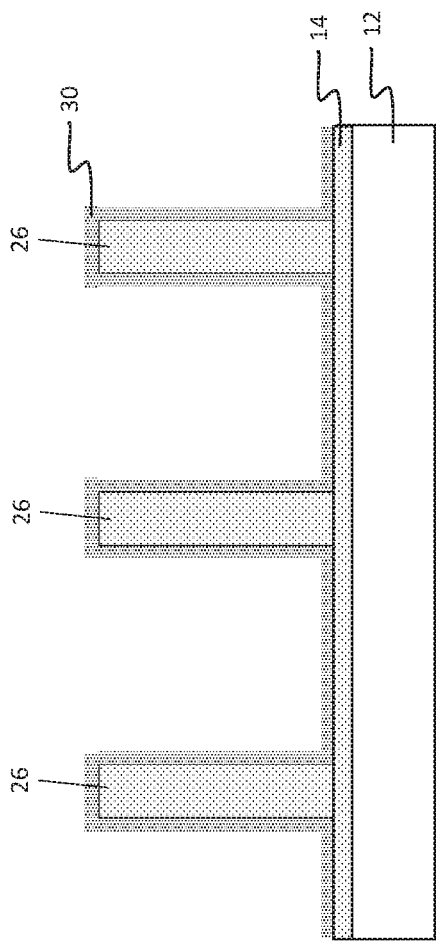
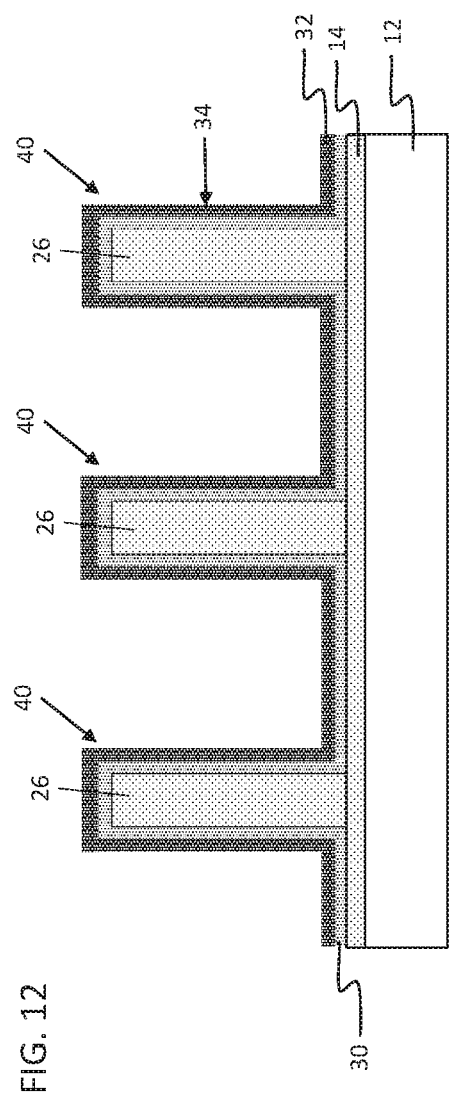

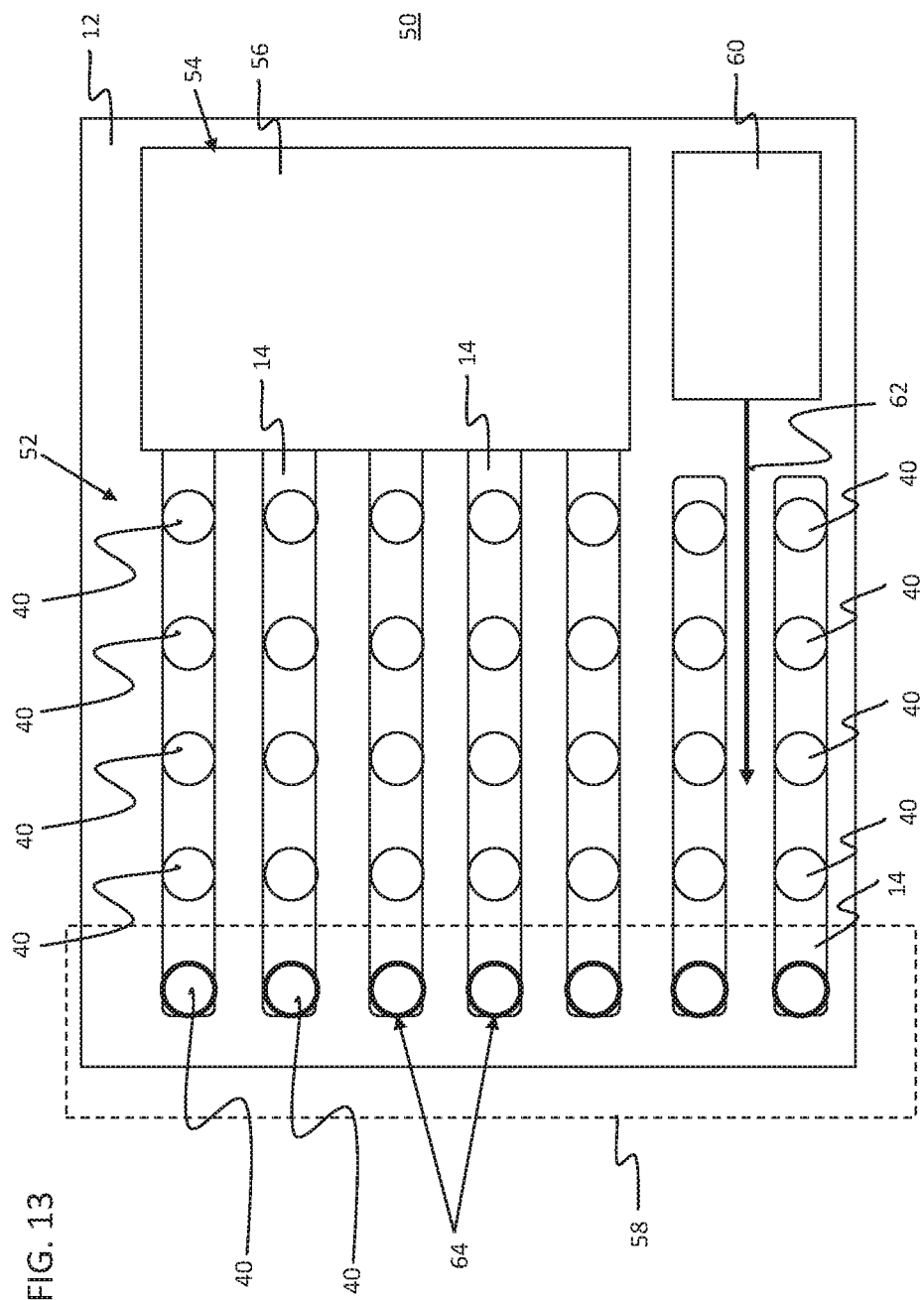

US 10,669,153 B2

NEURO-CHEMICAL SENSOR WITH SELECTIVELY PERMEABLE MEMBRANE ON NANO-ELECTRODE

BACKGROUND

Technical Field

The present invention generally relates to biosensing devices, and more particularly to devices and methods for detection or quantification of neurochemicals that employ a selectively permeable membrane to enable selective molecular interactions with a device electrode.

Description of the Related Art

Biosensors are components used in medical diagnostic systems. These devices detect and measure vital analytes in a number of ways. One common example of a commercial biosensor includes a glutamate quantification sensor. Electrodes employed in such devices need protection to prevent competing molecules from reacting at the electrodes. Polymer layers used for this protection typically possess thicknesses on the order of 5 microns. This thickness range hinders the ability to pinpoint local concentrations of glutamate.

SUMMARY

In accordance with an embodiment of the present invention, a biosensor includes an array of electrically conductive nanorods formed on a substrate. The nanorods each includes a nanoscale porous coating formed on a surface of the nanorods from silicon dioxide layers. An enzyme coating is bound to the porous coating.

Another biosensor includes a substrate and an electrically conductive layer formed on the substrate. Footings are formed on the electrically conductive layer. An array of electrically conductive nanorods where each nanorod is integrally formed with a respective footing at a base of the nanorod. The footings extend beyond a vertical sidewall of the nanorods.

A method for fabricating a biosensor includes forming nanorods on an electrically conductive layer; forming a nanoscale conformal layer over the nanorods by atomic layer deposition by depositing alternating layers of aluminum and silicon and oxidizing each alternating layer before forming the next alternating layer; and wet etching the conformal layer to remove aluminum oxide to form a porous coating.

These and other features and advantages will become apparent from the following detailed description of illustrative embodiments thereof, which is to be read in connection with the accompanying drawings.

BRIEF DESCRIPTION OF THE DRAWINGS

The following description will provide details of preferred embodiments with reference to the following figures wherein:

FIG. 11 is a cross-sectional view showing the substrate of FIG. 10 having the atomic layer deposited coating wet etched to form a porous or nanoporous coating formed on the metal layer and the nanorods in accordance with an embodiment of the present invention;

FIG. 12 is a cross-sectional view showing the substrate of FIG. 11 having a biocompatible coating including an enzyme formed on the porous or nanoporous coating in accordance with an embodiment of the present invention;

FIG. 13 is a plan schematic view showing a biosensor device having nanorods and circuits integrated on a substrate in accordance with an embodiment of the present invention.

DETAILED DESCRIPTION

Figure 1:
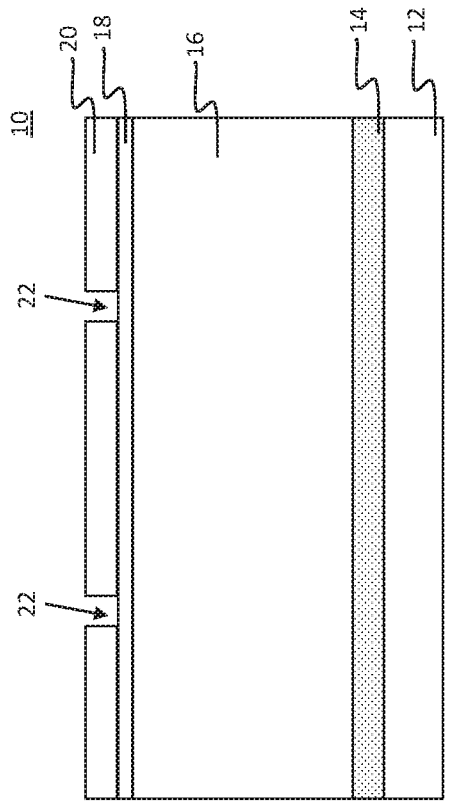
FIG. 1 is a cross-sectional view showing a substrate having a metal layer, organic planarizing layer, hard mask layer and patterned resist formed thereon for forming nanorods in accordance with an embodiment of the present invention.

In accordance with embodiments of the present invention, biosensors are employed for measuring the presence of one or more materials in the vicinity or in contact with the biosensors. In useful embodiments, a substrate having electronics or connections to electronics can include one or more nanorods. The nanorods can include inert metals, such as Pt or the like. The nanorods are vertically disposed and have a diameter or transverse width of between about 20 nm to about 3 microns, preferably between about 100 nm to about 500 nm, although other useful sizes are contemplated. The nanorods can be arranged in an array or other configuration on the substrate to promote collection of materials or enhance the presence of materials.

In one embodiment, the biosensors employ electrodes for glutamate quantification. The electrodes are formed as nanorods that include a selectively permeable membrane employed over the electrodes to prevent competing molecules from reacting at the electrode. The membranes can be coated with one or more polymer layers that can include a total thickness of about 5-40 nm. This increases the pinpoint accuracy or local concentrations of an analyte to be measured. The nanorods are employed as a part of a nanosensor (biosensor) where the nanorods are employed to pinpoint local concentrations of, e.g., glutamate. Conventional membrane coating processes are incompatible with nanometer scale electrodes.

In particularly useful embodiments, a new coating method and material are provided for the selectively permeable membranes on the nanorod electrodes. Atomic layer deposition (ALD) can be employed to form composite layers of, e.g., silicon oxide and aluminum oxide onto the nanorod electrode structures. Acid removal of the aluminum oxide layers can be performed to leave behind a porous silicon oxide membrane that functions as a filter to prevent biofouling of the nanorod electrodes. A permeability of the coating or membrane can be modified by adjusting the percent content of the Al. Self-assembled monolayers may also be attached to the porous membrane to modify permeability. In one embodiment, glutamate oxidase can be anchored to the electrode membrane with the use of multifunctional aldehydes. In one embodiment, electropolymerized layers of polypyrrole, poly(3,4-ethylenedioxythiophene) (PEDOT) and poly aniline, with the enzymes being embedded or anchored in these layers, can be employed.

It is to be understood that aspects of the present invention will be described in terms of a given illustrative architecture; however, other architectures, structures, substrate materials and process features and steps can be varied within the scope of aspects of the present invention.

It will also be understood that when an element such as a layer, region or substrate is referred to as being "on" or "over" another element, it can be directly on the other element or intervening elements can also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements can be present. In contrast, when an element is referred to as being "directly connected" or "directly coupled" to another element, there are no intervening elements present.

The present embodiments can include a design for an integrated circuit chip, which can be created in a graphical computer programming language, and stored in a computer storage medium (such as a disk, tape, physical hard drive, or virtual hard drive such as in a storage access network). If the designer does not fabricate chips or the photolithographic masks used to fabricate chips, the designer can transmit the resulting design by physical means (e.g., by providing a copy of the storage medium storing the design) or electronically (e.g., through the Internet) to such entities, directly or indirectly. The stored design is then converted into the appropriate format (e.g., GDSII) for the fabrication of photolithographic masks, which typically include multiple copies of the chip design in question that are to be formed on a wafer. The photolithographic masks are utilized to define areas of the wafer (and/or the layers thereon) to be etched or otherwise processed.

Methods as described herein can be used in the fabrication of integrated circuit chips. The resulting integrated circuit chips can be distributed by the fabricator in raw wafer form (that is, as a single wafer that has multiple unpackaged chips), as a bare die, or in a packaged form. In the latter case, the chip is mounted in a single chip package (such as a plastic carrier, with leads that are affixed to a motherboard or other higher level carrier) or in a multichip package (such as a ceramic carrier that has either or both surface interconnections or buried interconnections). In any case, the chip is then integrated with other chips, discrete circuit elements, and/or other signal processing devices as part of either (a) an intermediate product, such as a motherboard, or (b) an end product.

It should also be understood that material compounds will be described in terms of listed elements, e.g., SiGe. These compounds include different proportions of the elements within the compound, e.g., SiGe includes $Si_xGe_{1-x}$ where x is less than or equal to 1, etc. In addition, other elements can be included in the compound and still function in accordance with the present principles. The compounds with additional elements will be referred to herein as alloys.

Reference in the specification to "one embodiment" or "an embodiment", as well as other variations thereof, means that a particular feature, structure, characteristic, and so forth described in connection with the embodiment is included in at least one embodiment. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This can be extended, as readily apparent by one of ordinary skill in this and related arts, for as many items listed.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

Spatially relative terms, such as "beneath," "below," "lower," "above," "upper," and the like, can be used herein for ease of description to describe one element's or feature's relationship to another element(s) or feature(s) as illustrated in the FIGS. It will be understood that the spatially relative terms are intended to encompass different orientations of the device in use or operation in addition to the orientation depicted in the FIGS. For example, if the device in the FIGS. is turned over, elements described as "below" or "beneath" other elements or features would then be oriented "above" the other elements or features. Thus, the term "below" can encompass both an orientation of above and below. The device can be otherwise oriented (rotated 90 degrees or at other orientations), and the spatially relative descriptors used herein can be interpreted accordingly. In addition, it will also be understood that when a layer is referred to as being "between" two layers, it can be the only layer between the two layers, or one or more intervening layers can also be present.

It will be understood that, although the terms first, second, etc. can be used herein to describe various elements, these elements should not be limited by these terms. These terms are only used to distinguish one element from another element. Thus, a first element discussed below could be termed a second element without departing from the scope of the present concept.

Referring now to the drawings in which like numerals represent the same or similar elements and initially to FIG. 1, a partially fabricated biosensor device 10 is shown in accordance with one embodiment. The device 10 includes a substrate 12 having one or more layers formed thereon. The substrate 12 can include any suitable substrate structure, e.g., a bulk semiconductor, a semiconductor-on-insulator (SOI) substrate, etc. In one example, the substrate 12 can include a silicon-containing material. Illustrative examples of Si-containing materials suitable for the substrate 12 can include, but are not limited to, Si, SiGe, SiGeC, SiC and multi-layers thereof. Although silicon is the predominantly used semiconductor material in wafer fabrication, alternative semiconductor materials can be employed as additional layers, such as, but not limited to, germanium, gallium arsenide, gallium nitride, silicon germanium, cadmium telluride, zinc selenide, etc.

Since the present embodiments provide a device that can work remotely, the device 10 can include a substrate having powered circuitry for controlling the functions of the device 10. In this way, the substrate 12 can include control circuitry fabricated using known semiconductor processing techniques. Components can include transistors, metal lines, capacitors, logic gates or any other electronic components that permit the control of the nanorods and other structures to be formed in subsequent steps. In one useful embodiment, bipolar junction transistors (BJT) can be employed in the circuitry formed in the substrate 12. BJT devices can be employed to generate sub-nanosecond pulsing, as will be described.

A metal layer 14 is deposited on the substrate 12. The metal layer 14 can include a conductive but relatively inert metal, such as, e.g., Pt, Au, Ag, Cu, Jr, Ru, Rh, Re, Os, Pd, and/or their oxides (e.g., $IrO_2$, RuOx, etc.), although other metals, metal oxides and their alloys can be employed. The metal layer 14 can be formed by deposition using a sputtering process, chemical vapor deposition (CVD) process, atomic layer deposition (ALD), a plating process or any other suitable deposition process.

In one embodiment, an organic planarizing layer (OPL) 16 is formed on the metal layer 14. The OPL 16 can be formed by a spin-on process or otherwise deposited.

An etch stop layer or hard mask 18 can be deposited over the OPL 16. In one embodiment the etch stop layer 18 can include a metal, such as, e.g., Ti, Ta, etc. or a metallic compound such as, e.g., TiN, TaN, SiARC (a silicon containing organic ARC layer), TiARC (a titanium ARC), etc. A resist layer 20 is formed on the etch stop layer or hard mask 18. The resist layer 20 can be spun on. The resist layer 20 is patterned to form openings 22 that will be employed to form nanorods, as will be described.

Figure 2:
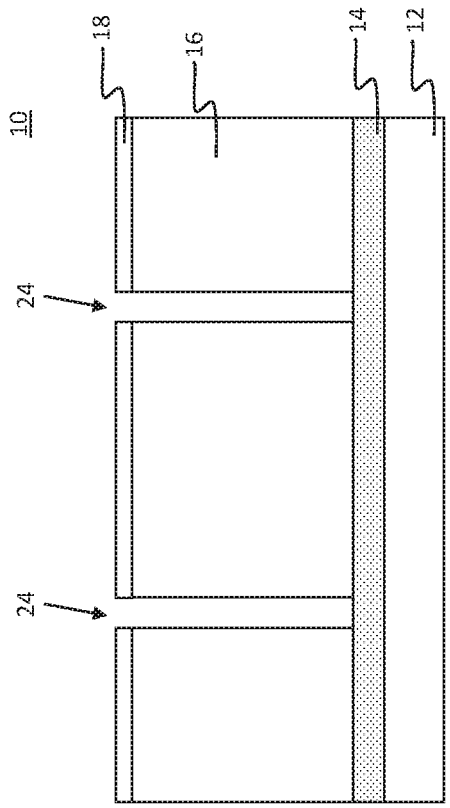
FIG. 2 is a cross-sectional view showing the substrate of FIG. 1 having the metal layer exposed by etching the organic planarizing layer in accordance with the hard mask layer and the patterned resist for forming nanorods in accordance with an embodiment of the present invention.

Referring to FIG. 2, an etch process is performed to open up the etch stop layer 18. In one embodiment, a reactive ion etch (RIE) process can be performed to expose the OPL 16 through the openings 22 (FIG. 1). Then, a reactive ion etch (RIE) is performed to etch through the OPL 16 to expose the metal layer 14 and form trenches 24 in accordance with the resist 20 and/or the etch stop layer or hard mask 18. The trenches 24 provide locations for the formation of nanorods. The etch of OPL 16 should be minimized to maintain small critical dimensions (CDs) for the hole or trench 24 to be plated.

Figure 3:
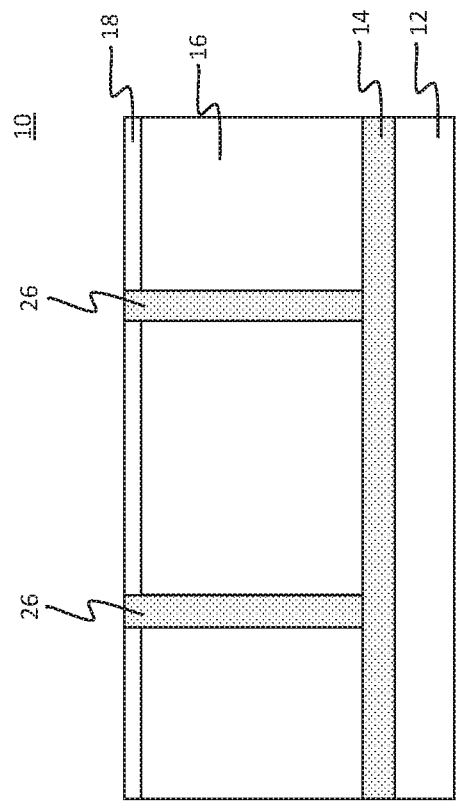
FIG. 3 is a cross-sectional view showing the substrate of FIG. 2 having nanorods plated and connecting to the metal layer and planarized to the hard mask layer for forming nanorods in accordance with an embodiment of the present invention.

Referring to FIG. 3, a metal deposition process is performed and can include a plating process, CVD, ALD, or the like. The metal of the deposition process preferably includes a same metal as employed in metal layer 14. In one particularly useful embodiment, the metal of layer 14 and the metal used in nanorods 26 can include Pt, Ag, Ag, Cu, etc. although other metals, alloys, metal oxide or conductive materials can be employed. The nanorods 26 can be annealed with the OPL 16 present or with the OPL 16 removed. If the hard mask 18 includes, e.g., Ti or TiN, the hard mask 18 can be removed with hydrogen peroxide aqueous solution, or if it is Ti oxide or TiARC, it can be removed with diluted HF, as wet etching is simpler and easier to control than planarization processes such as, e.g., a chemical mechanical polish (CMP). However, a planarization process, such as, e.g., CMP, can be employed if other hard mask materials are employed. The hard mask 18 is removed down to the OPL 16. Then, the OPL 16 can be removed by, e.g., an $O_2$ plasma etch or $N_2/H_2$ plasma etch, etc. with a mild wet clean to remove residues.

Figure 4:
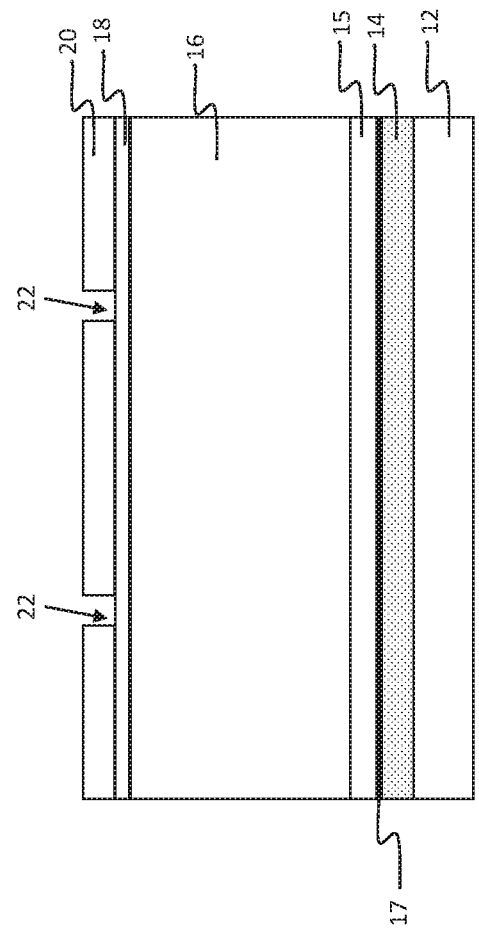
FIG. 4 is a cross-sectional view showing a substrate having a metal layer, an undercut layer, an organic planarizing layer, a hard mask layer and a patterned resist formed thereon for forming profile nanorods in accordance with an embodiment of the present invention.

Referring to FIG. 4, in accordance with a particularly useful embodiment, the biosensor device 10 can be formed with an optimized profile. The profile can include a larger lateral base to increase support strength, improve electrical flow by reducing resistively and provide additional conductive material, among other advantages. The substrate 12 can include any suitable substrate structure, e.g., a bulk semiconductor, a semiconductor-on-insulator (SOI) substrate, etc. The nanorods 26 can be bound more strongly to the metal layer 14 below. One issue that arises with a single stack of OPL is that the dimension of the etched hole becomes narrow at the bottom as a result of the limitations of the RIE process. By adding a layer under the OPL, we can add a wet etch step after the RIE, which will selectively etch the layer under the OPL, but not etch the OPL. In this way, the size of the patterned hole can be expanded at the bottom, and when the nanorod is plated into the hole, it will fill this area and be larger at the base of the pillar.

The metal layer 14 is deposited on the substrate 12. The metal layer 14 can include a conductive but relatively inert metal, such as, e.g., Pt, Au, Ag, Cu, etc. or other suitable metals or alloys. The meal layer 14 can be formed by deposition using a sputtering process, chemical vapor deposition (CVD) process, atomic layer deposition (ALD), a plating process or any other suitable deposition process.

An undercut layer 15 is deposited on the metal layer 14. The undercut layer 15 can include for example, one or more of a lift-off resist (LOR), anti-reflection coating (ARC), e.g., a developable bottom ARC (DBARC), a silicon oxide or a silicon on glass (SOG) layer that also can be employed to assist in removing the OPL 16 in subsequent processing. While the undercut layer 15 provides profile control, ease of removal of the OPL layer 16 can be a secondary goal in cases where lift-off processes are possible.

In some examples, where the OPL 16 includes a thickness of about 800 nm, the LOR can be about 100 nm, the DBARC can be about 50 nm, the silicon oxide can be about 50 nm, etc. Other dimensions are also contemplated.

In some embodiments, a capping layer 17 can be employed between the metal layer 14 and the undercut layer 15. For example, platinum can mix with silicon oxide during the OPL coat and bake steps, leading to difficulty in etching an oxide undercut layer 15. A capping film or layer 17 of TaN or TiN, for example, can prevent the mixing of the metal film with the silicon oxide film. In other embodiments, OPL 16 is formed on the undercut layer 15. The OPL 16 can be formed by a spin-on process or other deposition process.

The hard mask 18 can be deposited over the OPL 16. In one embodiment the etch stop layer 18 can include a metal, such as, e.g., Ti, Ta, etc. or a metallic compound such as, e.g., TiN, TaN, etc. The resist layer 20 is formed on the etch stop layer or hard mask 18. The resist layer 20 can be spun on. The resist layer 20 is patterned to form openings 22 that will be employed to form nanorods, as will be described.

Figure 5:
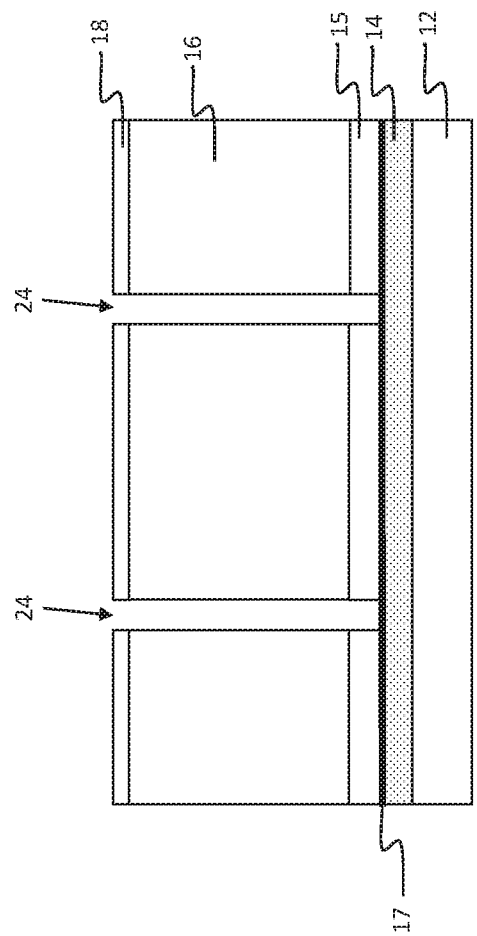
FIG. 5 is a cross-sectional view showing the substrate of FIG. 4 having the metal layer exposed by etching the organic planarizing layer and the undercut layer in accordance with the hard mask layer and the patterned resist for forming nanorods in accordance with an embodiment of the present invention.

Referring to FIG. 5, an etch process is performed to open up the etch stop layer 18. In one embodiment, a wet etch process using, e.g., HF can be performed to expose the OPL 16 through the openings 22 (FIG. 1). Then, a reactive ion etch (RIE) is performed to etch through the OPL 16 and the undercut layer 15 to expose the metal layer 14 and form trenches 24 in accordance with the resist 20 and/or the hard mask 18. The trenches 24 provide locations for the formation of nanorods. The etch of OPL 16 should be minimized to maintain small critical dimensions (CDs) for the hole or trench 24 to be plated.

Figure 6:
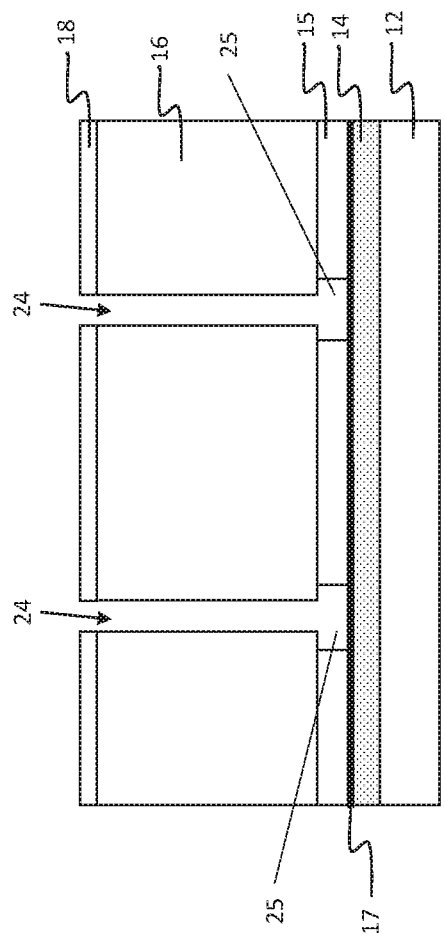
FIG. 6 is a cross-sectional view showing the substrate of FIG. 5 having the undercut layer laterally etched for forming undercuts in accordance with an embodiment of the present invention.

Referring to FIG. 6, an etch process is performed to laterally etch undercuts 25 in the undercut layer 15. A tetramethylammonium hydroxide (TMAH) etch can be employed (e.g., for LOR, DBARC) or HF etch (e.g., for silicon oxide, SOG, etc.). If HF is employed, the hard mask 18 can be removed at the same time as the undercut formation.

Figure 7:
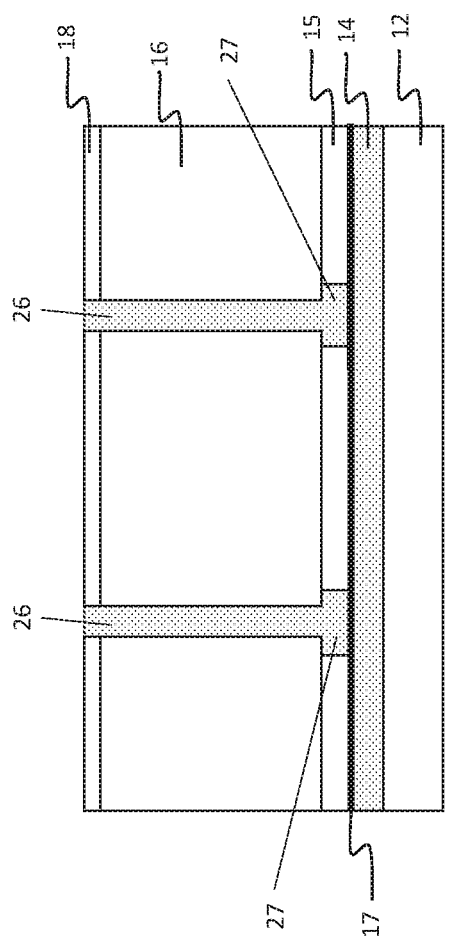
FIG. 7 is a cross-sectional view showing the substrate of FIG. 6 having nanorods and footings plated and planarized to the hard mask layer for forming nanorods in accordance with an embodiment of the present invention.

Referring to FIG. 7, a metal deposition process is performed and can include a plating process, CVD, sputtering or the like. The metal of the deposition process preferably includes a same metal as employed in metal layer 14. In one particularly useful embodiment, the metal of layer 14 and the metal used in nanorods 26 can include Pt, although other metals or alloys can be employed. The nanorods 26 include footings 27 formed in the undercuts 25 (FIG. 6). The nanorods 26 can be annealed with the OPL 16 present or with the OPL 16 removed. The etch stop layer 18 can be removed by a wet etch process or by a planarization process, such as, e.g., a chemical mechanical polish (CMP), down to the OPL 16. The undercut layer 15 can be removed with the OPL 16 or in addition to the OPL 16.

Figure 8:
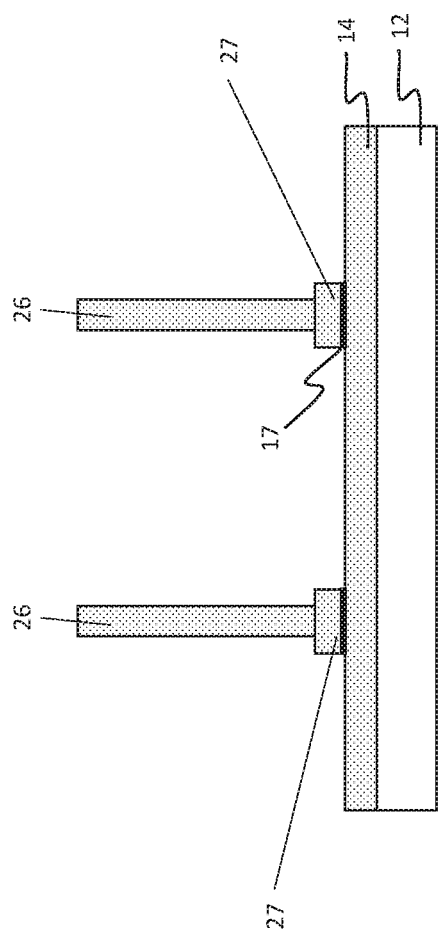
FIG. 8 is a cross-sectional view showing profile nanorods with footings formed on the metal layer in accordance with an embodiment of the present invention.

Referring to FIG. 8, the nanorods 26 and footings 27 are ready for continued processing. The nanorods 26 include the footing 27, which has a base that extends beyond a vertical sidewall of the nanorod 26. The footing 27 can be concentric or have a different shape than the circumference of the nanorods 26. The nanorods 26 can be arranged in any configuration suitable for creating a biosensor, e.g., an array, with uniform or non-uniform spacings, of nanorods with profile control optimized for chemical sensors, neurological implants or other applications. The nanorods 26 described hereinafter will employ the structure of FIG. 9; however, the structure of FIG. 8 can be employed, and these structures are completely interchangeable.

Figure 9:
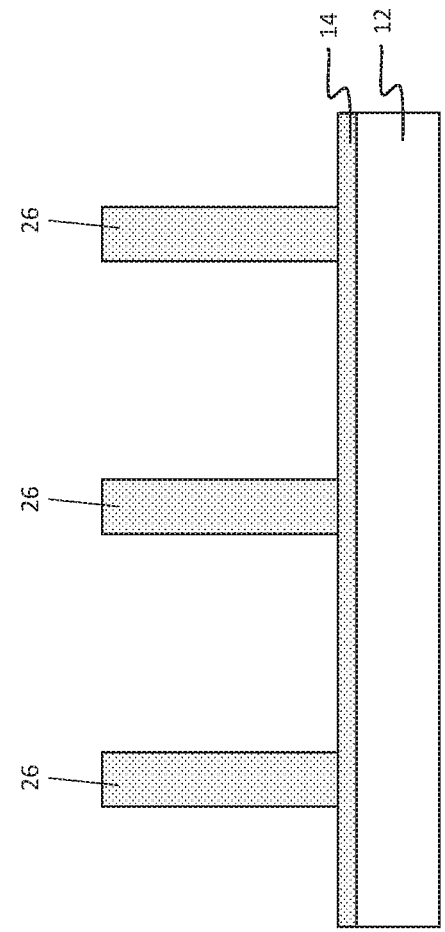
FIG. 9 is a cross-sectional view showing nanorods formed on the metal layer using the process in FIGS. 1-3 in accordance with an embodiment of the present invention.

Referring to FIG. 9, after the removal of the OPL 16 and the anneal of the nanorods 26, the nanorods 26 are ready for continued processing from the straight profile of FIG. 3. The nanorods 26 can be arranged in any configuration suitable for creating a biosensor, e.g., an array with uniform or non-uniform spacings, etc.

An anneal, after the OPL (16) is removed, mixes the nanorod 26 (and/or its footing 27) with the metal layer 14, and welds the nanorod 26 to the metal layer 14, which further enhances mechanical stability of the nanorod 26. The anneal can be at least 300 degrees C., and since silicon oxide is more stable than the organic layers, a dielectric such as silicon oxide, silicon nitride, titanium oxide, aluminum oxide, hafnium oxide and similar materials may be preferable to the DBARC or LOR underlayers, which are organic and less stable at temperatures above 300 degrees C.

Some dielectrics, like silicon oxide, are not stable on the Au or Pt surface of the metal layer 14, but intermix with the metal to some extent. In such cases, a liner material, such as, e.g., TiN, TaN, $TiB_2$, can be added over the over the metal layer 14 to act as a barrier to intermixing.

Figure 10:
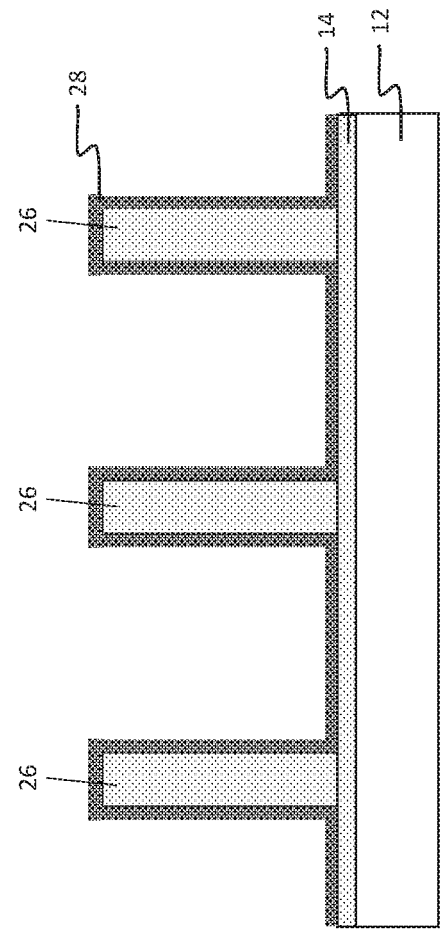
FIG. 10 is a cross-sectional view showing the substrate of FIG. 9 having an atomic layer deposited coating formed on the metal layer and the nanorods in accordance with an embodiment of the present invention.

Referring to FIG. 10, a coating 28 is formed over the nanorods 26 and the metal layer 14. The coating 28 is formed using ALD, which will be processed to prepare a nanoporous $SiO_2$ film by mixing ALD formed alumina and silica in multiple layers. Each cycle of the ALD process can deposit one of Si or Al with an oxidation after each deposition cycle to form a respective oxide (e.g., $SiO_2$ or $Al_2O_3$). The ALD reagent for forming Al can include $AlMe_3$ while the reagent for forming the $SiO_2$ can include $(Me_2N)_3SiH$ (where Me is a methyl group). The ALD process can include a plurality of cycles to deposit a plurality of layers. The plurality of layers can include a large number (e.g., two to several hundred). The plurality of layers form the coating 28, which includes $SiO_2$ and $Al_2O_3$ having a total thickness of between about 2 nm to about 50 nm. While other dimensions are contemplated, the coating 28 preferably includes a nanoscale thickness.

Referring to FIG. 11, a wet etch process is performed on the coating to selectively remove the $Al_2O_3$ from coating 28. The wet chemical etch can include, e.g., etching with phosphoric acid or hydrofluoric acid. The wet etch results in a nanoporous coating 30 including thin $SiO_2$ layers. The nanoporous coating 30 functions as a filter permitting limited access paths to the nanorods 26 through the porosity of the coating 30, which is an atomic scale porosity. The porosity of the nanoporous coating can be between about 5% to about 80%. The nanoporosity can be controlled by adjusting the amount of Al in the coating 28 (FIG. 10) during formation. For example, the greater the Al content the greater the porosity.

Referring to FIG. 12, a binding of an enzyme 32 is provided on the nanoporous coating 30 for the electrode surface of the nanorods 26 and the metal layer 14. The enzyme 32 can include any useful enzyme or biomaterial. In one embodiment, glutamate oxidase can be employed as the enzyme 32. The enzyme 32 can be bound to the nanoporous coating 30 by a crosslinker, e.g., an aldehyde cross linker. In other embodiments, electropolymerized layers can be formed, e.g., polypyrrole, poly(3,4-ethylenedioxythiophene) (PEDOT), poly aniline, etc. These layers can include enzymes embedded therein during or after formation.

The enzyme 32 can generate a signal upon contact with an analyte, e.g., biofouling cells. The cross-linking agent can include one or more hydrophilic cross-linking agent. The enzyme 32 is immobilized in the nanoporous coating 30 via the hydrophilic cross-linking agent, which increases hydration and creates hydrophilic channels or pathways for reactive species. A biocompatible membrane, comprising the enzyme 32, the nanoporous coating 30 and the hydrophilic cross-linking agent provides enhanced diffusion of reactive species, increased sensitivity and inhibits biofouling.

A surface layer 34 can be formed for bio-compatibility and/or to adjust or modify the permeability of the porous coating 30 and 32. In one embodiment, a self-assembled monolayer (SAM) is formed as a surface layer 34 to mimic cell membrane materials. The SAM layer can include organic molecules or molecular assemblies formed on the surface by adsorption or chemisorption to form large ordered domains, which can form two-dimensional supramolecular networks or SAMs having a head group (e.g., thiols, silanes, phosphonates, etc.), tail (covalent bonds, Si, C, O, etc.) and functional end group (radicals, R, including, e.g., —OH, —NH$_2$, —COOH, or —SH groups). The head groups assemble together on the surface, while the tail groups assemble in a liquid suspension far from the surface. Areas of close-packed molecules nucleate and grow until the surface is covered in a single monolayer forming anti-biofouling electrodes 40 in accordance with the present principles.

Referring to FIG. 13, a device 50 for inhibiting biofouling is illustratively shown in accordance with one exemplary embodiment. The device 50 includes an array 52 of electrodes 40. The array 52 includes uniform spacings between electrodes 40; however, non-uniform spacings can be employed. A circuit 54 can include an array of transistors and/or other circuit components (e.g., integrated into the substrate 12) configured to activate or selectively activate electrodes. The circuit 54 can be integrated into the substrate 12 using semiconductor processing techniques. The circuit 54 can include a high voltage power source, e.g., if the device 50 is implantable in the body. Alternatively, the circuit 54 can connect to a separate external power source.

The circuit 54 can be controlled using a controller circuit 56 that generates signals to control which electrodes 40 are activated. The high voltage (e.g., 5 to 100 volts (or more)) can be programmed to activate the electrodes 40 using a patterned metal layer 14 to connect to the electrodes 40 in localized areas to prevent cell growth over specific regions of the array 52 or the whole array 52. The activation of the electrodes can prevent cell growth or selectively kill cells in these regions or parts of cells in the region.

Device 50 can also include a biosensor that employs biological recognition properties for selective detection of various analytes or biomolecules. The biosensor 50 can generate a signal or signals that quantitatively relate to a concentration of the analyte on or near the electrodes 40. To achieve a quantitative signal, a recognition molecule or combination of molecules can be immobilized at the electrodes 40, which convert the biological recognition event into a quantitative response.

In some embodiments, the nanorod electrodes 40 can include a biocidal material coating 64, such as, e.g., cellular poisons, star polymers, nanoparticles, etc. bound to the nanorod electrodes 40 in selected regions 58. In another embodiment, a radiation source 60, such as, e.g., a laser, nuclear radiation source or the like can direct radiation 62 to selectively kill cells in specific regions of the device 50. The device 50 can oscillate between measuring cycles and cycles to inhibit biofouling using, e.g., high voltage pulses or the like.

The device 50 can be made disposable after use. The substrate 12 and other components can be coated or shielded to prevent contamination to the host from materials of the device 50.

Figure 14:
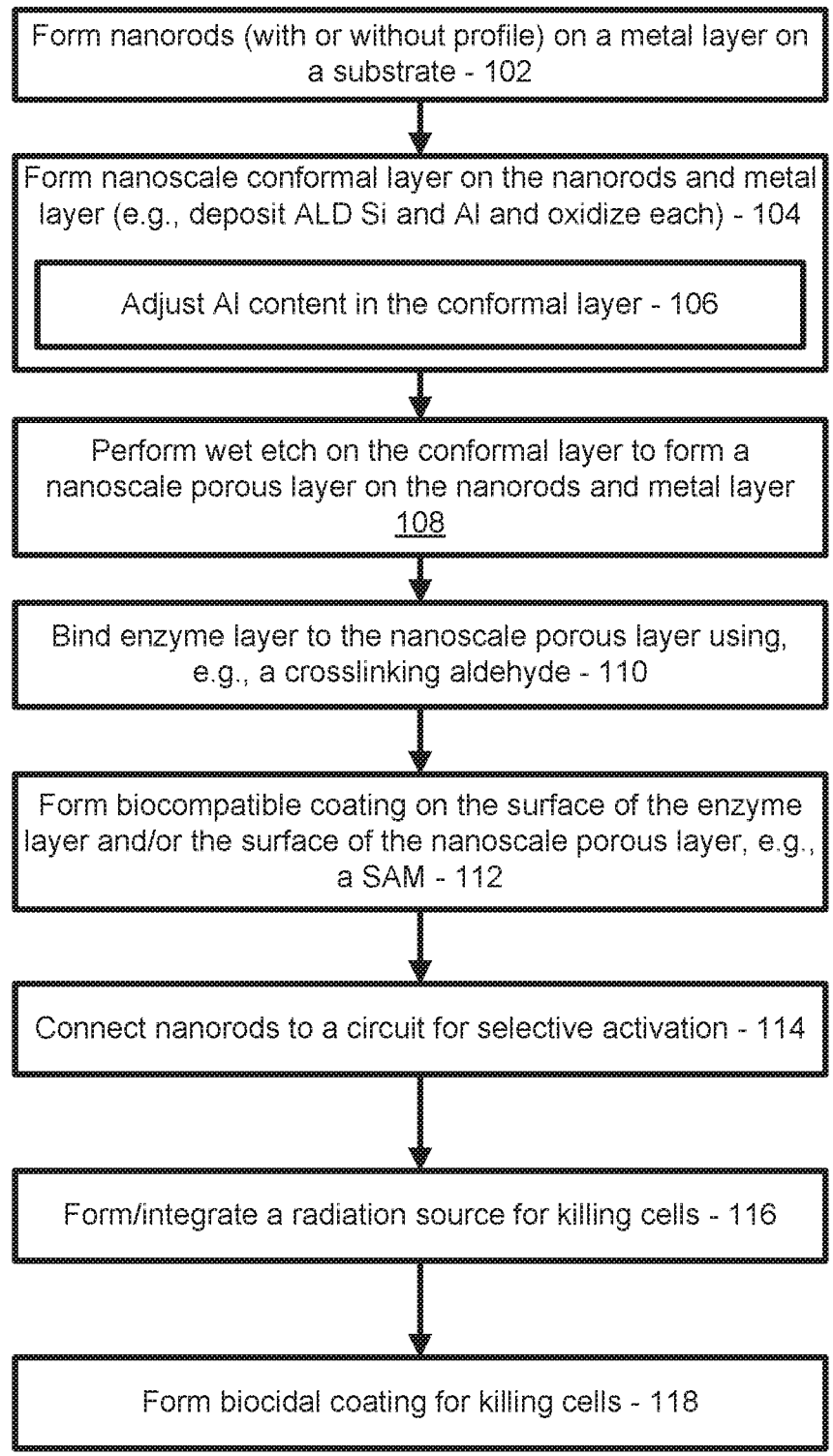
FIG. 14 is a block/flow diagram showing methods for fabricating biosensors in accordance with embodiments of the present invention.

Referring to FIG. 14, methods for fabricating biosensors are illustratively shown and described. In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In block 102, nanorods are formed on a metal layer. The metal layer on which the nanorods are formed can be patterned to provide electrical connections to the nanorods or groups of nanorods. In useful embodiments, the nanorods 26 and footings 27 can also be employed. Profiles (footings 27) can be employed by forming an undercut layer and laterally etching the undercut layer to form undercuts. The footings are formed in the undercuts with the formation of the nanorods.

In block 104, a nanoscale conformal layer is formed over the nanorods by atomic layer deposition by depositing alternating layers of, e.g., aluminum and silicon and oxidizing each alternating layer before forming the next alternating layer. The process can include depositing one layer including one of aluminum and silicon, oxidizing the one layer, depositing a next layer including the other of aluminum and silicon, oxidizing the next layer and repeating until a thickness of the conformal layer is achieved. It should be understood that two or more layers of one type of material (e.g., Si or Al) can be formed before oxidizing or that two or more alternating layers can be formed before oxidizing, as needed. It should also be understood that while Si and Al are preferred materials, other material combinations can be employed to form a porous coating or membrane.

In block 106, the conformal layer can have an aluminum content adjusted during ALD deposition to adjust the permeability of the porous coating. The amount of aluminum or the number of cycles/layers formed can be adjusted to adjust the aluminum content.

In block 108, a wet etch is performed on the conformal layer to remove aluminum oxide to form a porous or nanoporous coating. The wet etch selectively removes the aluminum oxide leaving a porous form of the silicon oxide. The wet etch can include use of phosphoric acid or hydrofluoric acid.

In block 110, in one embodiment, an enzyme layer can be bound to the porous coating. The enzyme can be bound by crosslinking the enzyme using an aldehyde. In one embodiment, the enzyme includes glutamate oxidase.

In block 112, a biocompatible coating can be formed on the porous or nanoporous coating and/or on the enzyme using, e.g., a self-assembled monolayer (SAM). In one embodiment, the SAM can be employed to modify permeability of the porous coating, e.g., by its selection and/or processing.

In block 114, the nanorods are connected to a circuit to provide selective activation of the nanorods as electrodes. This connection can be performed contemporaneously with other processing steps. The circuit can include an integrated circuit formed within the same substrate as the nanorods are formed on. Alternately, the circuit or chip can connect or be integrated with the substrate with the nanorods. Metal paths can be formed by patterning the metal layer on which the nanorods are formed.

In block 116, a radiation source or device (e.g., a laser, nuclear radiation source, etc.) can be formed or integrated in the device with the nanorod electrodes to selectively kill cells in specific regions of the device.

In block 118, in some embodiments, a biocidal coating can be formed over at least some of the nanorods including structural shaped particles (e.g., biocidal nanoparticles) or poisons to destroy cells in contact therewith.

Having described preferred embodiments for neurochemical sensors with selectively a permeable membrane on nano-electrodes (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A biosensor, comprising:
    an array of electrically conductive nanorods formed on a substrate, the nanorods each including:
        a nanoscale porous coating formed on a surface of the nanorods from a plurality of silicon dioxide layers; and
        an enzyme coating bound to the porous coating; and
    a circuit formed in the substrate to control activation of electrodes formed by the nanorods.

2. The biosensor as recited in claim 1, wherein the enzyme coating includes glutamate oxidase.

3. The biosensor as recited in claim 1, wherein the substrate includes a semiconductor material.

4. The biosensor as recited in claim 1, further comprising a biocompatible coating formed on the enzyme coating.

5. The biosensor as recited in claim 4, wherein the biocompatible coating includes a self-assembled monolayer (SAM).

6. The biosensor as recited in claim 1, further comprising a biocidal coating formed over at least some of the nanorods including shapes or poisons to destroy cells in contact therewith.

7. A biosensor, comprising:
    a substrate;
    an electrically conductive layer formed on the substrate;
    footings formed on the electrically conductive layer; and
    an array of electrically conductive nanorods, each nanorod integrally formed with a respective footing at a base of the nanorod, the footings extending beyond a vertical sidewall of the nanorods.

8. The biosensor as recited in claim 7, wherein the substrate includes a semiconductor material and a circuit is formed in the substrate to control activation of electrodes formed by the nanorods.

9. The biosensor as recited in claim 7, further comprising:
    a nanoscale porous coating formed on a surface of the nanorods from a plurality of silicon dioxide layers; and
    an enzyme coating bound to the porous coating.

10. The biosensor as recited in claim 9, further comprising:
    a biocompatible coating formed on the enzyme coating.

* * * * *